United States Patent

Nogami

[11] Patent Number: 6,001,157
[45] Date of Patent: Dec. 14, 1999

[54] ADDITIVE FOR ANTIFOULING PAINT

[76] Inventor: Hideaki Nogami, 2-6-12-303 Ohmiya, Chuo-ku, Fukuoka-shi, Fukuoka 810-0013, Japan

[21] Appl. No.: 09/221,564

[22] Filed: Dec. 28, 1998

[51] Int. Cl.$^6$ .............................. C09D 5/16; A01N 59/00
[52] U.S. Cl. .................. 106/18.3; 106/15.05; 106/18.31; 106/286.1; 106/286.2; 106/286.3; 106/286.4; 106/286.5; 106/286.6; 106/286.7; 424/601; 424/602
[58] Field of Search ............................. 106/15.05, 18.31, 106/18.3, 286.1, 286.2, 286.3, 286.4, 286.5, 286.6, 286.7; 424/601, 602

[56] References Cited

PUBLICATIONS

Chemical Abstract No. 88–138066 which is an abstract of Japanese Patent Specification No. 52–136231 (Nov. 1977).
Chemical Abstract No. 117:235881 which is an abstract of Japanese Patent Specification No. 04–141292 (May 1992).
Chemical Abstract No. 118:236015 which is an abstract of Japanese Patent Specification No. 04–325571 (Nov. 1992).
Chemical Abstract No. 119:252215 which is an abstract of Japanese Patent Specification No. 05–070716 (Mar. 1993).
Chemical Abstract No. 129:246254 which is an abstract of Japanese Patent Specification No. 10–237918 (Sep. 1998).
WPIDS Abstract No. 96–439751 which is an abstract of Japanese Patent Specification No. 08–218004 (Aug. 1996).

*Primary Examiner*—Anthony J. Green
*Attorney, Agent, or Firm*—Hedman, Gibson & Costigan, P.C.

[57] ABSTRACT

An additive for antifouling paint uses a mixture made from a negative ion emitting compound powder, such as monazite powder, and tourmaline powder.

2 Claims, 1 Drawing Sheet

ADDITIVE FOR ANTIFOULING PAINT

BACKGROUND OF THE INVENTION

1. Field of the Invention

The present invention relates to an additive for antifouling paint, and in particular relates to an additive for antifouling paints which makes it possible to prevent marine organisms and marine algae from adhering the bottom of ships made of various materials including steel ships, FRP (fiber reinforced plastic) ships and wooden ships, submerged structures, various fishing nets including aquaculture nets, buoys, and industrial water system facilities.

2. Description of the Prior Art

In the prior art, an antifouling paint containing rosin or organic tin has been painted onto ships, submerged structures, fishing nets and the like in order to stop corrosion and drag due the adhesion of marine organisms such as barnacles, mytilus coruscus, algae and the like. Further, an antifouling paint containing rosin or organic tin has also been applied to aquaculture nets in order to prevent the destruction of marine products due to the adhesion of various marine organisms.

In this connection, ships cruising the ocean face the problem of damage due the adhesion of marine organisms on the ship bottom. Further, because the carpet-like layer of algae and shellfish adhering to all parts of the ship below the ocean surface, including the ship bottom, creates a huge drag force, a variety of adverse effects occur. For example, at an output of 80%, a ship having absolutely no adhered bodies will have a cruising speed of 10 knots, but the same ship having a large amount of adhered bodies will only have a cruising speed of 5~6 knots. Consequently, the greater output required of ships having a large amount of adhered bodies places a huge stress on the engine, and over time this can damage the engine. In particular, because a cruising ship will experience a large drag force due to the adhesion of marine organisms on ships, there will be (1) an increase in the negative load placed on the engine, (2) an increase in fuel consumption, and (3) damage to the ship itself.

In order to counter such damage, the bottom and sides of ships are painted with a special paint. This paint has a slippery surface like that of eel skin, and this property makes it difficult for bodies to adhere to such painted areas. In particular, in recent years the progress of research development in the field of paints has produced a paint that slowly dissolves over time (hydrolysis type paint) and a paint that slowly wears away over time (a self-abrasion type paint), but even these special paints are not able to sufficiently eliminate the adhesion of bodies such as oyster shells, algae and ulva. Moreover, surface painted with such paints must be repainted before the paint dissolves or wears away. Furthermore, in addition to containing paint components (e.g., organic tin) which are highly toxic to marine life, such paints form one cause of ocean pollution. For these reasons, the use of these special types of paints is not preferred.

Further, repainting is required due to the peeling off and wearing away of paint on ships and the like, and in the case of a small ship, repainting must be carried out once every 3~6 months, while in the case of a large ship such as a 100m-class ship, repainting must be carried out once a year. In this regard, when ships are to be repainted, the adhered bodies must first be removed, and then after surface soil and salt has been washed away, the step of repainting is carried out, and for a large ship the step of removing adhered bodies can itself be an arduous task, with all steps requiring about one week to complete.

It is not an exaggeration to say that the world economy is supported by the flow of goods transported by ships from various countries. In this connection, painting is an absolute requirement for any and all ships, whether they be tankers, freighters or passenger ships, and all ships are faced with the problem of bodies such as oyster shells, algae and the like adhering to their hulls.

The painting of ships addresses the problems caused when organisms living in the ocean adhere and grow on the hulls of ships, namely, lowering of speed due to increased drag, increased fuel consumption, greater engine loads, shorter engine life, and rapid damage to the hull due to increased hull vibration. The main cause of these serious problems is the adherence of marine organisms such as oyster shells, algae, ulva and the like, and in order to reduce such adherence, the following products have tested. Namely, a (1) self-abrasion type paint and (2) ahydrolysis type paint have been tested.

(1) Self-Abrasion Type Paint

By utilizing the driving force of the ship, self-abrasion type paint is designed to peel away and fall off, with adhered bodies such as oyster shells, algae and ulva falling off together with the paint that falls off, and one example of a self-abrasion type paint is a paint which uses a copolymer containing organic silicon.

However, in the case where self-abrasion type paint is applied to wooden ships or the like, the lack of a flat bottom means there are grooves where it is difficult for the paint to peel away, and this makes it impossible to prevent the adhesion of organisms such as oyster shells, algae, ulva and the like.

(2) Hydrolysis Type Paint

Hydrolysis type paints are designed to be hydrolyzed by sea water (i.e., salt water), with an organic tin compound or the like being eluted as the paint vehicle dissolves in sea water, and as this antifouling agent is eluted, organisms such as oyster shells, algae, ulva and the like fall off into the ocean together with such paint compounds.

However, while hydrolysis type paint can be painted onto FRP ships, it can not be used for aluminum ships because of the hazardous compounds created by chemical reactions between the paint and aluminum. Further, because hydrolysis type paints utilize reactions with seawater (i.e., salt water), they are not effective in lakes or rivers (i.e., in fresh water).

Moreover, because the (1) self-abrasion type paint will peel away and the (2) hydrolysis type paint has components that will wash away, both paints (1) and (2) have a relatively short binding period of approximately 6 months. In response to this, various paint manufacturers have expended a great deal of effort in developing ways to prevent as much as possible the adhesion of organisms and ways to extend the binding period of paints, but no effective solutions have been found yet.

SUMMARY OF THE INVENTION

It is an object of the present invention to solve the problems described above by providing an additive to antifouling paint which makes it possible to reduce the adhesion of marine organisms such as oyster shells, algae and the like, improve fuel economy, extend the binding period of the paint, and simply the work of painting, without being a toxic source of ocean pollution.

The additive for antifouling paint according to the present invention can be used for ships, ocean structures, various nets including aquaculture nets, buoys and industrial water system facilities, and has a main component comprised of a mixture formed from tourmaline powder and a powder compound which normally emits negative ions such as monazite powder.

Each of the powders mentioned above has an average particle diameter of 3~10 μm, and the mixture thereof forms an additive for antifouling paint. Further, the mixture which forms an additive for antifouling paint has a negative ion emitting powder content of 40%~60% by weight with respect to a tourmaline content of 60%~40% by weight.

One representative example of a monazite compound which emits negative ions is cerium, lanthanum phosphate mineral. For example, the monazite used in the present invention has a F content of 8.7% by weight (hereafter, the following content numbers will mean \% by weight), a MgO content of 0.62, a $Al_2O_3$ content of 0.72, a $SiO_2$ content of 5.2, a $P_2O_5$ content of 2.3, a $SO_3$ content of 4.4, a Cl content of 1.1, a $K_2O$ content of 0.074, a CaO content of 1.8, a Kr content of 0.019, a SrO content of 1.2, a BaO content of 4.5, a $La_2O_3$ content of 23, a $CeO_2$ content of 34, a $Pr_6O_{11}$ content of 3.3, an $Nd_2O_3$ content of 8.1, a $Sm_2O_3$ content of 0.76, and a $ThO_2$ content of 0.16. However, the monazite compound used by the present invention is not limited to these components and these content ratios, and it is of course possible to use other components and content ratios so long as the monazite compound is capable of emitting negative ions. In this connection, Table 1 shows the ion measurement results for the case where the monazite compound described above is used. These negative ions have a sterilizing force which prevents the growth of algae and the adhesion of shells such as barnacles, mytilus coruscus and the like.

The powdered negative ion emitting compound such as monazite powder or the like and the tourmaline powder (described below) are given an average particle diameter of 3~10 μm. If the particle diameter of the powders is greater than 10 μm, the additive in the antifouling paint painted on the hull or the like will cause a reduction in speed, the adhesiveness with the paint will be weakened, and the work required for painting will be made difficult. On the other hand, if the particle diameter is smaller than 3 μm, the ship will output greater speed, but the use of such small diameter particles will result in higher costs. For these reasons, an average particle diameter smaller than 3 μm or greater than 10 μm is not preferred.

As for tourmaline, it is a cyclosilicate mineral containing boron. The general composition formula is represented by $XY_9B_3Si_6O_{27}(O, OH, F)_4$ (where X=Ca, Na, K, Mn, Y=Mg, Fe, Al, Cr, Mn, Ti, Li). There are various types of tourmaline, including Dravite magnesium oxide tourmaline (obtained from metamorphic rock and pegmatite), Schori iron tourmaline (obtained from pegmatite), and Elbaite lithia tourmaline (obtained from scaly lithia mica). In addition to adsorbing negative electrons by means of electrodes, tourmaline has properties that display piezoelectric and pyroelectric effects. Further, tourmaline has water electrolysis and surface activity effects, and when tourmaline comes into contact with water, a discharge immediately takes place in the water. Thus, the surrounding water undergoes electrolysis, in which the molecules of water are dissociated into hydrogen ions and hydroxide ions. Then, the hydroxide ions combine with surrounding water molecules and change into a surface active compound known as hydroxyl ions ($H_3O_2$), and by forming a monomolecular film with such hydroxyl ions, it is possible to generate a surface active effect.

In this connection, Table 1 shows the contents and amounts of minerals (greisen) for one example tourmaline used in the present invention, but it should be noted that the present invention is not limited to these contents and ratio values.

TABLE 1

| Components Identified by X-line Diffraction | | Sample Name: Tourmaline(greisen) |
|---|---|---|
| Mineral Type | Chemical Formula | Determined Amounts |
| ① | $(NaK)Ca(SiAl)_6O_{12}Cl$ | ◉ 35.9 |
| ② | $Na_{0.8}Mg_3Al_6B_3O_9Si_6O_{18}(OH)_4$ | ◉ 21.9 |
| ③ | $Na_4SnBe_2(Si_3O_9).2H_2O$ | ○ 17.6 |
| ④ | $Al_2SiO_4(FOH)_2$ | Δ 10.0 |
| ⑤ | $Na_2MgSiO_4$ | ▲ 8.0 |
| ⑥ | $SiO_2$ | ▲ 6.6 |

*Percentage is calculated by the X-line diffraction strength ratio, with the detemined ratio changing due to the diffraction strength of each crystal.
◉ Large amount is present
○ An amount is present
Δ A small amount is present
▲ Some is present but can not be confirmed
X None is present Now, the reason why the present invent ion uses a mixture containing a negative ion emitting compound, such as monazite, and tourmaline is because the use of a single powder of a negative ion emitting compound can not adequately prevent bodies such as algae and shells from adhering to hulls and the like, while the use of a mixture containing the two powders described above acts synergistically to increase the negative ion emitting effect, and this in turn increases the antifouling effect. Further, as was described above, this mixture has a negative ion emitting compound powder content of 40%~60% by weight with respect to a tourmaline powder content of 60%~40% by weight, with equal ratios for both powders being preferred. Furthermore, when mixing the negative ion emitting compound powder and the tourmaline powder, ceramic powder or mineral powder may also be mixed in so long as such addition does not hinder the properties described above. In particular, a powdered compound that emits far infrared radiation has a positive influence on the antifouling effect.

The amount of the additive according to the present invention that should be added to antifouling paint for ships and the like is 5%~20% by weight with respect to antifouling paint in the amount 100% by weight. If the amount of the additive lies outside this range, the intended effect of the present invention will not be adequately achieved. Further, if too much of the additive according to the present invention is added to the antifouling paint, the adhesiveness with the paint will be weakened. Preferably, the additive is present in the amount roughly 10% by weight with respect to antifouling paint in the amount 100% by weight. In principal, the additive according to the present invention can be used with hydrolysis type paint, self-abrasion type paint, and various other types of paint, but is not applied to antifouling paints which contain hazardous compounds connected with ocean pollution, such as organic tin.

DETAILED DESCRIPTION OF THE PREFERRED EMBODIMENTS

Specific Embodiment 1

Figure 1:
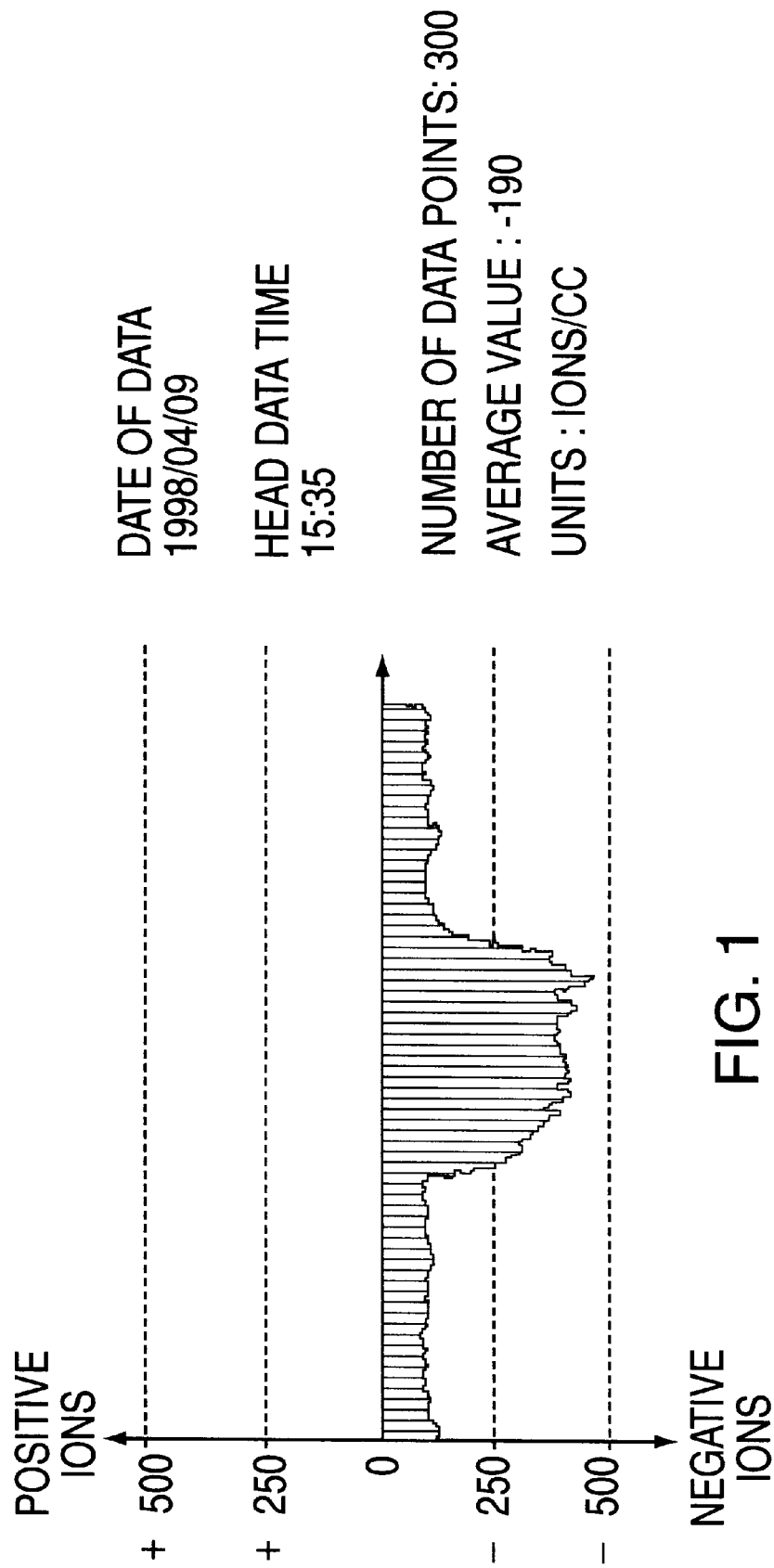
FIG. 1 is a graph showing the number of negative ions generated by the monazite used in the present invention.

An additive containing equal proportions of monazite powder of above-mentioned element and tourmaline powder mentioned in Table 1 (both having an average particle diameter of 6 μm) was added to "Rubucks AF" by Chuugoku Toryou Co. (a resin enamel paint containing xylene at 20%~30% by weight) in the amount 10% by weight with respect to paint in the amount 100% by weight. This paint was then applied to a FRP ship at an application amount 190 g/$m_2$. In carrying out this application, the following operations were carried out. First, the ship was taken out of the water and placed on land. Next, adhered bodies were removed from the surface of the hull. In this regard, adhered marine organisms, soil, oil and the like were removed by scraping and wiping with thinner and the like. Next, the ship was washed with fresh water. Then, after the salt was removed, the ship was sufficiently dried. In the case of areas where the FRP surface was exposed, such areas were made even with sandpaper. Then, the ship was painted once, and after five hours had elapsed, was painted again. After such painting was completed, drying was carried out for more than 12 hours at 20° C. Then, after drying was completed, the ship was returned to water.

After two months had elapsed since the completion of the above-described painting operations, an inspection of the ship revealed that there was no algae, such as ulva, and no shells, such as oyster shells, on the surface of the hull.

As described above, the present invention produces the following characteristic effects:

(1) The adhesion of marine organisms such as oyster shells, algae, ulva and the like can be substantially reduced due to the function of a negative ion.

(2) The paint binding period can be made substantially longer than that of the prior art.

(3) Fuel consumption can be made more economical than that of the prior art.

(4) An antifouling effect is produced in the ocean (i.e., salt water) and in lakes and rivers (i.e., fresh water).

Now, when a ship is painted with a prior art paint, such ship needs to be repainted every 6 months or every year. In contrast to this, a ship painted with a paint containing the additive according to the present invention needs to be repainted only every 2 or 3 years, and this vast improvement makes it possible to reduce costs. Further, in addition to extending the paint binding time, the additive according to the present invention produces many other significant effects, such as maintaining the cruising speed of the ship, lessening the load on the engine, and reducing the amount of damage to the hull.

What is claimed is:

1. An additive for antifouling paint, comprising:
    a mixture made from monazite powder and tourmaline powder wherein the monazite powder content is 40%–60% and the tourmaline powder content is 60%–40% by weight.

2. The additive for antifouling paint according to claim 1, wherein the monazite powder and the tourmaline powder each have an average particle diameter of 3~10 μm.

* * * * *